United States Patent [19]

Bartfai

[11] Patent Number: 5,283,321

[45] Date of Patent: Feb. 1, 1994

[54] POLYPEPTIDE COMPOUND WHICH BINDS TO GLYCO-CONJUGATES AND TO ARTIFICIAL PERTUSSIS TOXIN ANTIGEN

[75] Inventor: Tamas Bartfai, Stocksund, Sweden

[73] Assignee: Trion Forskning-och Utvecklings Aktiebolag, Sollentuna, Sweden

[21] Appl. No.: 375,004

[22] PCT Filed: Dec. 21, 1987

[86] PCT No.: PCT/SE87/00619

§ 371 Date: Jul. 18, 1989

§ 102(e) Date: Jul. 18, 1989

[87] PCT Pub. No.: WO88/04665

PCT Pub. Date: Jun. 30, 1988

[30] Foreign Application Priority Data

Dec. 22, 1986 [SE] Sweden .................. 8605513
Feb. 24, 1987 [SE] Sweden .................. 8700761

[51] Int. Cl.$^5$ ............................ C07K 7/00
[52] U.S. Cl. ................... 530/326; 530/402; 530/403; 530/404; 530/405
[58] Field of Search ........... 424/92; 530/326, 403, 530/325, 326, 327, 328, 329, 330, 403, 404, 405

[56] References Cited

U.S. PATENT DOCUMENTS 4,883,761 11/1989 Keith et al. ................ 435/320.1
5,000,952 3/1991 Steinman et al. ................ 424/92

FOREIGN PATENT DOCUMENTS 121249 10/1984 European Pat. Off. .......... 424/92

OTHER PUBLICATIONS

Mehra et al. (1986) Proc. Natl. Acad. Sci. 83, 7013–7017.
Frank et al. (1984) Infect. Immune 46(1), 195–201.
Sato et al. (1984) Infect. Immune. 46(2) 422–428.
Perera et al. (1986) J. Gen. Microbiol. 132, 553–556.

Primary Examiner—Robert A. Wax
Assistant Examiner—R. Keith Baker
Attorney, Agent, or Firm—Bacon & Thomas

[57] ABSTRACT

A polypeptide of the formula $$H-X^1-Gln-Thr-Art-Ala-Asn-Pro-Asn-Pro-Tyr-Thr-Ser-Arg-Arg-Ser-Val-Ala-Ser-X^2-Y$$

in which $X^1$ and $X^2$ each represents an optional coupling-facilitating amino acid residue, and Y represents —OH or —NH$_2$, and an artificial compound in free or carrier-associated form with the capability of binding to glyco-conjugates, especially immunoglobulins, which compound is chosen from the group consisting of said peptide and functional analogues and functional derivatives thereof, are disclosed. Additionally, there is described an artificial pertussis toxin antigen, which mainly consists of at least one peptide sequence reacting with antibodies induced by the native pertussis toxin selected from the above polypeptide and parts thereof. The above described artificial pertussis toxin antigen is included as a diagnostic antigen in a diagnostic immunoassay kit for the determination of antibodies induced by the native pertussis toxin in a sample of biological fluid, and as an immunizing component in a vaccine composition against whooping cough, respectively. Furthermore, there is described an intradermal skin test composition comprising the above described artificial pertussis toxin antigen.

3 Claims, No Drawings

POLYPEPTIDE COMPOUND WHICH BINDS TO GLYCO-CONJUGATES AND TO ARTIFICIAL PERTUSSIS TOXIN ANTIGEN

The present invention relates to a new polypeptide, to an artificial compound, selected from the new peptide and functional analogues and derivatives of the peptide, in free or carrier-associated form with the capability of bindning to glyco-conjugates, especially immunoglobulins, to artificial pertussis toxin antigens, which mainly consist of peptide sequences reacting with antibodies induced by the native pertussis toxin selected from the new polypeptide and parts thereof, to a diagnostic immunoassay kit comprising as a diagnostic antigen, said antigens reacting with antibodies induced by the native pertussis toxin, to a vaccine composition comprising as an immunizing component antigens selected from said antigens reacting with antibodies induced by the native pertussis toxin, and to an intradermal skin test composition comprising antigens selected from said antigens reacting with antibodies induced by the native pertussis toxin.

BACKGROUND

In the field of immunology it is well known that most biological organisms produce specific proteins which selectively and specifically recognize various protein and/or carbohydrate structures. Examples of such specific proteins derived from bacteria are Protein A and Protein G which both bind to certain immunoglobulins from various species. Examples of such specific proteins derived from plants or lower invertebrates are so-called lectins which bind to carbohydrate structures of immunoglobulins and other glyco-conjugates. Examples of such lectins are Concanavalin A, Wheat germ agglutinin, Phytohaemagglutinin and Helix pomatia lectin.

Each of the above mentioned specific proteins bind to a specific group of protein structures and/or carbohydrate structures.

The present invention provides an artificial compound which has the capability of binding to glyco-conjugates, especially immunoglobulins.

Up to now no peptide antigens constituting part of pertussis toxin have been identified in the art. Since such antigens have not been provided, it has not been possible to develop diagnostic immunoassay kits comprising such antigens as diagnostic antigens nor to develop vaccines against whooping cough based on such antigens.

Diagnosis of whooping cough with the aid of antigens directed against *Bordetella pertussis* antibodies or proteins produced by *B. pertussis* have been published, but as diagnostic antigen there has been used fimbrial hemagglutinin (see e.g. Granström, M., Granström, G., Lindfors, A, and Askelöf, P. 1982. Serologic diagnosis of whooping cough by an enzyme-linked immunosorbent assay using fimbrial hemagglutinin as antigen. J. Infect. Dis. vol 146: 741-745), or sonicated *B. pertussis* bacteria (see e.g. Goodman, Y. E., Wort, A. J. and Jackson, F. L. 1981. Enzyme-linked immunosorbent assay for detection of pertussis immunoglobulin A in nasopharyngeal secretions as an indicator of recent infection J. Clin. Microbiol. vol. 13: 286-292, and Viljanen, M. K., Ruuskanen, O., Granberg, C. and Salmi, T. T. 1982. Serological diagnosis of pertussis: IgM, IgA and IgG antibodies against *Bordetella pertussis* measured by enzyme-linked immunosorbent assay. Scand. J. Infect. Dis. vol. 14: 112-117).

As is well known in the art currently used vaccines against whooping cough are in USA and many other countries based on inactivated *Bordetella pertussis* bacteria. M. Pittman proposed 1979 that whooping cough was mediated by an exotoxin (pertussis toxin) (see Pittman, M. 1979. Pertussis toxin: The cause of the harmful effects and prolonged immunity of whooping cough. A hypothesis. Rev. Infect. Dis. vol. 1:401-412) and in Japan acellular vaccines comprising inactivated pertussis toxin are currently in use.

Recently the nucleotide sequence of pertussis toxin was published (Locht, C. and Keith, J. M., 1986. Pertussis Toxin Gene: Nucleotide Sequence and Genetic Organization, Science, vol. 232, p. 1258-1264). In this article the authors suggest i.a. that synthetic oligopeptides that include protective epitopes also will be useful in the development of a new generation of vaccines, but there is no teaching or suggestion of such epitopes.

Another recently published article concerning pertussis toxin genes is: Nicosia, A., Perugini, M., Franzini, C., Casagli, M. C., Borri, M. G., Antoni, G., Almoni, M., Neri, P., Ratti, G., and Rappuoli, R., 1986. Cloning and sequencing of the pertussis toxin genes: Operon structure and gene duplication. Proc. Natl. Acad. Sci. USA, vol. 83, 4631-4635. In this publication it is stated i.a. that "Manipulation of the toxin gene by genetic engineering could be a way to produce large amounts of detoxified protein". This is merely a suggestion and no manipulated toxin gene is disclosed.

Yet another publication in this field is: Engström, O., Rodmalm, K., Jörnvall, H., Lundquist, G., Kálmán, M., Simonscits, A., Bartfai, T., Löfdahl, S., and Askelöf, P., 1986. Characterization of the N-terminal structure of pertussis toxin subunit S1 and hybridization of oligodeoxyribonucleotide probes with *Bordetella pertussis* DNA fragment, FEMS Microbiology Letters, vol. 36, 219-223. Also this article makes suggestions, namely, "The gene may also be introduced into other organisms for production of toxin. Sequencing of the gene would allow synthesis of peptides corresponding to the antigenic epitopes of the toxin and hence to the development of a synthetic pertussis vaccine." However, the antigenic epitopes of the pertussis toxin have not been identified, synthesized nor tested.

As regards intradermal skin test compositions, such compositions for testing immunity against pertussis are hitherto not described in the art.

DESCRIPTION OF THE INVENTION

In one aspect of the invention there is provided a new polypeptide of the formula H—$X^1$—Gln—Thr—Arg—Ala—Asn—Pro—Asn—Pro—Tyr—Thr—
—Ser—Arg—Arg—Ser—Val—Ala—Ser—$X^2$—Y in which $X^1$ and $X^2$ each represents an optional coupling-facilitating amino acid residue, and Y represents —OH or —$NH_2$.

Examples of suitable optional amino acid residues are —Lys— and —Cys—. These optional amino acid residues facilitate the coupling of a carrier, such as bovine serum albumin, to said polypeptide.

The peptide according to the invention has been synthesized in accordance with per se known solid phase techniques.

As is well known in this field a peptide is synthesized either in acid (COOH) or amide (CONH$_2$) form depending on available resin-bound starting amino acid.

In another aspect of the invention there is provided an artificial compound in free or carrier-associated form with the capability of binding to glyco-conjugates, which compound is chosen from the group consisting of the polypeptide of the formula H—X$^1$—Gln—Thr—Arg—Ala—Asn—Pro—Asn—Pro—Tyr—Thr——Ser—Arg—Arg—Ser—Val—Ala—Ser—X$^2$—Y in which X$^1$ and X$^2$ each represents an optional coupling-facilitating amino acid residue, and Y represents —OH or —NH$_2$; and functional analogues and functional derivatives thereof.

When the compound according to the invention is in carrier-associated form it can be associated to any carrier to which it can be linked by physical/chemical interaction, such as covalent binding, ionic binding, hydrogen binding or hydrophobic binding. Examples of such carriers are mineral carriers, e.g. glass, aluminium hydroxide, calcium phosphate, etc., plastic surfaces, e.g. microplates, beads, etc., lipids, liposomes, carbohydrates, amino acids, peptides, proteins, membranes or fractions thereof and whole cells or fractions thereof.

The expression "glyco-conjugate" as it is used in this specification and claims is intended to include glycoproteins, glycolipids, peptidoglycanes and proteoglycanes whether they are in free or carrier-associated form (both in vivo and in vitro).

The binding mechanism is not yet ascertained, but it is firmly believed that the compound according to the invention binds to the glyco portion of the above defined glyco-conjugates, even though there may also occure other sites on the glyco-conjugates which may be of equal importance in the interaction between said compound and the glyco-conjugates. It is further believed that it is the binding conformation of the peptide of the invention in aqueous solution (pH-values ranging from 1 to 13) that is responsible for this specific binding to the glyco-conjugates.

In view of the above the compound of the invention can be selected from a wide variety of compounds as long as they have a similar capability of binding to glyco-conjugates (e.g. glycoproteins) as the peptide of the invention.

Thus the expression "functional analogues" of the peptide of the invention is intended to cover i.a. shorter or longer monomers or polymers of the peptide (e.g. functional fractions or fragments, or polymers of fractions or fragments of the peptide) with or without substitution of one or several amino acid residues for other amino acid residues, as long as the analogues have a similar capability of binding to glyco-conjugates (especially glycoproteins e.g. immunoglobulins) as the peptide of the invention.

Further the expression "functional derivatives" of the peptide of the invention is intended to cover compounds having a similar capability of binding to glyco-conjugates (especially glycoproteins e.g. immunoglobulins) as the peptide of the invention. Examples of such compounds are compounds having essentially the structure of the peptide according to the invention, but having one or several amino acid residues substituted for other chemical groups, i.e. organic as well as inorganic molecules or elements.

Since it is believed that it is the binding conformation of the peptide of the invention in aqueous solution that is responsible for the binding of said peptide to the defined glyco-conjugates, it follows that the functional analogues and functional derivatives (of the peptide of the invention) should comprise at least one conformation corresponding essentially to the binding conformation of said peptide in aqueous solution.

In a preferred embodiment of the invention there is provided an artificial compound in free or carrier-associated form with the capability of binding to immunoglobulins, which compound is chosen from the group consisting of the polypeptide of the formula H—X$^1$—Gln—Thr—Arg—Ala—Asn—Pro—Asn—Pro—Tyr—Thr——Ser—Arg—Arg—Ser—Val—Ala—Ser—X$^2$—Y in which X$^1$ and X$^2$ each represents an optional coupling-facilitating amino acid residue, and Y represents —OH or —NH$_2$; and functional analogues and functional derivatives thereof.

The polypeptide and the compound according to the invention have highly interesting properties which make them extremely useful in the field of immunology.

The compound of the invention binds to glyco-conjugates, especially glycoproteins e.g. immunoglobulins, and can thus be used in enzyme-associated form in enzyme-linked immunosorbent assay (ELISA) instead of conjugates conventionally used in such assays.

The compound of the invention can be used as a general sorbent for glyco-conjugates, e.g. immunoglobulins or other immunologically active substances, e.g. $\beta$2-microglobulin. As a sorbent it can be applied to or utilized for extracorporeal body fluids (in vivo) using plasmapheresis to clear the body fluid from immune complexes. Other examples of the usefulness of said compound as a sorbent in plasmapheresis is in the treatment of such diseases as allergies, leukemias and AIDS.

As a sorbent it can further be used (in vitro) in purifying poly- and monoclonal antibodies and other immunologically active substances.

Further the compound of the invention in carrier-associated form has a wide applicability (in vitro) in the field of immunochemistry. The carrier can specifically be a label (marker), such as gold particles, colloidal gold, enzymes (e.g. alkaline phosphatase or horseradish peroxidase), avidin, biotin or some radioactive isotope, (e.g. iodine).

The compound of the invention binds to immunologically active cells and hence it can be used in carrier-associated form for targeting (in vivo). Examples of carriers in this respect are various pharmaceuticals, cytostatic agents and hormones. An application of targeting of special interest is targeting of artificial, synthetic and subunit vaccines to immune-competent cells.

The compound according to the invention can further be used to block receptors on cell membranes, a property which makes said compound useful for immunosuppression in patients receiving allografts, such as kidney, liver or bone-marrow.

A further interesting property of the compound of the invention in free form is that it behaves as a lymphocyte activating factor (LAF) and induces mitosis in cells and thus the compound possesses a strong adjuvant activity.

In another aspect of the invention there is provided an artificial pertussis toxin antigen, which mainly consists of at least one peptide sequence reacting with antibodies induced by the native pertussis toxin selected from the group consisting of the polypeptide H—X$^1$—Gln—Thr—Arg—Ala—Asn—Pro—Asn—Pro—Tyr—Thr——Ser—Arg—Arg—Ser—Val—Ala—Ser—X$^2$—Y in which X$^1$ and X$^2$ each represents an optional coupling--facilitating amino acid residue, and Y represents —OH or —NH$_2$; and parts thereof.

The polypeptide according to the invention is able to induce antibodies, which react with the native toxin, in animals. Hence it can be considered as an antigen. Being an antigen, the polypeptide according to the invention is likely to include shorter peptide sequences which on their own induce antibodies which react with the native pertussis toxin. The artificial pertussis toxin antigen reacting with antibodies induced by the native pertussis toxin according to the invention does not necessarily comprise more than one such shorter peptide sequence being part of the polypeptide of the invention together with a carrier, even though it preferably comprises several such shorter peptide sequences.

The expression "artificial pertussis toxin antigen", as it is used in this specification and appended claims, is contemplated to include pertussis toxin antigens that have been produced in an artificial manner, i.e. contrived through human effort and not by natural causes detached from human agency. Even though the peptide sequences constituting, or constituting part of, the artificial pertussis toxin antigen according to the invention have been chemically synthesized according to per se known solid-phase technique, said peptide sequences can be produced using some other techniques, e.g. synthesis in liquid phase by coupling one amino acid to the next in known manner, degradation, cloning etc, and it is intended that the expression "artificial" should cover products produced by any such technique.

The word "comprises" is used, in this specification and appended claims, to indicate that something is included, but that that something does not necessarily constitute the only thing included.

The expression "mainly consists of" in conjunction with "peptide sequences reacting with antibodies induced by the native pertussis toxin" is used to indicate that the ability of the artificial pertussis toxin antigen to react with antibodies induced by the native pertussis toxin derives from said peptide sequences".

The word "carrier" should be interpreted broadly, and the carrier can be anything to which the peptide in question can be linked by physical/chemical interaction, such as covalent binding, ionic binding, hydrogen binding or hydrophobic binding. Examples of such carriers are mineral carriers, e.g. aluminium hydroxide, calcium phosphate, etc., plastic surfaces, e.g. microplates, beads, etc., lipids, liposomes, carbohydrates, amino acids, peptides and proteins.

In still another aspect of the invention there is provided a diagnostic immunoassay kit for the determination of antibodies induced by the native pertussis toxin in a sample of biological fluid. The kit comprises as a diagnostic antigen at least one antigen selected from the artificial antigens reacting with antibodies induced by the native pertussis toxin according to the invention. Depending on the immunoassay used for the determination of antibodies induced by the native pertussis toxin the kit may comprise other suitable reagents, such as a carrier to which said diagnostic antigen is coupled, a positive standard serum sample, a negative standard serum sample, an enzyme conjugate, such as alkaline phosphatase or peroxidase, substrate for the enzyme conjugate, such as paranitrophenylphosphate, agar or agarose gel, radioactivly labelled antigen, buffer solutions and/or washing solutions. Optionally all the reagents in the kit are contained in separate sealed test tubes or vials marked with specific labels.

The sample of biological fluid is preferably a nasopharyngeal secretion, saliva, blood or serum sample from an animal, e.g. a human.

Examples of immunoassays in which the kit according to the invention can be used are ELISA (enzyme-linked immunosorbent assay), Immunodiffusion, Radioimmunoassay (RIA), and Immunoelectrophoresis (IE).

When ELISA (enzyme-linked immunosorbent assay) is used the kit according to the invention will comprise
a) a diagnostic antigen of the invention
b) optionally a carrier for said diagnostic antigen
c) optionally a positive standard serum sample
d) optionally a negative standard serum sample
e) an enzyme conjugate
f) optionally a substrate for said enzyme conjugate
g) optionally buffer solution(s), and
h) optionally washing solution(s).

When immunodiffusion or immunoelectrophoresis (IE) is used the kit according to the invention will comprise the same as for ELISA, with the exception of items e) and f). Instead there is needed a gel, such as agar or agarose gel, but such a gel is normally not included in the kit, since it is commonly available.

When radioimmunoassay (RIA) is used the kit according to the invention will comprise the same as for ELISA, with the exception of items e) and f), which will be substituted for radioactively labelled antigen. Optionally there may also be included a solution for the precipitation of radioactively labelled antigen bound to antibodies, such as trichloroacetic acid or secondary antibodies.

In a further aspect of the invention there is provided a vaccine composition, which as an immunizing component comprises at least one antigen selected from the artificial pertussis toxin antigens reacting with antibodies induced by the native pertussis toxin, according to the invention, preferably in an amount effective to protect a subject from the disease whooping cough, and a nontoxic pharmaceutically acceptable carrier and/or diluent. The carrier is a carrier which has been defined herein above, and the diluent may be a conventional diluent used in the art, such as saline solution. The vaccine composition accordning to the invention may further comprise an antigen adjuvant in an amount which together with the amount of said antigen is effective to protect a subject from the disease whooping cough. Examples of commonly used adjuvants in vaccines for humans are so-called mineral carriers, e.g. phosphate or hydroxide of calcium or aluminium, to which the antigen in question is adsorbed. An example of commonly used veterinary vaccine adjuvant is Freund's Complete Adjuvant. The vaccine composition may additionally comprise buffer(s) and/or preservative(s) as appropriate, and suitable buffers and preservatives are disclosed in e.g. US Pharmacopoeia.

In still a further aspect of the invention there is provided an intradermal skin test composition, which comprises at least one antigen selected from the artificial pertussis toxin antigens reacting with antibodies induced by the native pertussis toxin, according to the invention, in an amount effective to produce an immunological skin reaction at a specific antibody titre in a subject, and a nontoxic pharmaceutically acceptable carrier and/or diluent. The skin test composition according to the invention may further comprise buffer(s) and/or preservative(s), as appropriate.

Useful carriers, diluents, buffers and preservatives are defined herein above.

SYNTHESIS OF THE PEPTIDE ACCORDING TO THE INVENTION

Solid-phase (Merrifield) synthesis of the peptide according to the invention has been performed in conventional manner, by coupling the amino acids to one another, whereby peptide bonds are formed, starting with a solid phase (resin) to which the C-terminal of the first amino acid is coupled, whereupon the C-terminal of the next amino acid is coupled to the N-terminal of the first amino acid, etc. Finally, the built-up peptide is released from the solid phase.

Specifically the following peptide was synthesized:

H—Lys—Gln—Thr—Arg—Ala—Asn—Pro—As-
n—Pro—Tyr—Thr——Ser—Arg—Ar-
g—Ser—Val—Ala—Ser—OH

Synthesis of the peptide fragments was achieved using a Biosearch Sam Two (Biosearch, Inc. California USA) peptide synthesis machine using version 2.38 of Biosearch's peptide synthesis automation software for t-BOC amino acids. The standard (default) coupling constants were used for one gram of starting material (degree of substitution=0.33 meq/g).

The resin used for the synthesis of the peptide was a standard Merrifield Resin. The suitably protected amino acids were:

| | |
|---|---|
| Boc—Ala—OH (Boc—L-Alanine) | Boc—Arg(Tos)—OH (a-Boc—N-Tosyl-L-Arginine) |
| Boc—Asn—OH (Boc—L-Asparagine) | Boc—Gln—OH (Boc—L-Glutamine) |
| Boc—Lys(CL—Z)—OH (Boc-e-o-Chloro-Benzyl-oxycarbonyl-L-Lysine) | Boc—Pro—OH (Boc—L-Proline) |
| Boc—Ser(Bzl)—OH (Boc—O-Benzyl-L-Serine) | Boc—Thr(Bzl)—OH (Boc—O-Benzyl-L-Threonine) |
| Boc—Tyr($Cl_2$—Bzl)—OH (Boc—O-2,6-Dichloro-benzyl-L-Tyrosine) | Boc—Val—OH (Boc—L-Valine) |

As to the details regarding amino acid concentration, solvent volumes, reaction times etc, the recommendations of the manufacturer (Biosearch) were followed.

Specifically the following chemicals listed below were use in the synthesis, cleavage and purification of the synthetic peptide.

| SUBSTANCE | GRADE | SUPPLIER |
|---|---|---|
| Acetyl imidazole | p.a. | Aldrich |
| Dimethyl formamide | p.a. | Fluka |
| Diisopropylethyl amine | Double-distilled from 1 g/l ninhydrin, then 5 g/l KOH. First 10% destillate discarded. | Aldrich |
| Hydroxybenzyl triazole | p.a. | Aldrich |
| Methylene chloride | HPLC | Fisons (UK) |
| Ninhydrin | p.a. | Aldrich |
| Potassium hydroxide | p.a. | |

-continued

| SUBSTANCE | GRADE | SUPPLIER |
|---|---|---|
| t-Boc amino acids | | Bachem |
| Hydrogen fluoride | | AGA |
| Resorcinol | | |
| Dimethyl sulfide | | |
| Hydroxybenzyl triazole | p.a. (synthesis) | Aldrich |
| Trifluoroacetic acid | sequanal (HPLC) | Aldrich |
| Acetonitrile | HPLC | Rathburn |
| Acetic acid | p.a. | Merck |
| Diethyl ether | | Fluka |

The completed resin-bound peptide was removed from the synthesis chamber and rinsed with methanol, and dried to constant weight under vacuum.

Cleavage of the Peptide from the Resin Support

Portions (0.5 g) of the washed and dried resin--bound peptide was transferred to a cylindrical polytetrafluoroethylene (PTFE) chamber containing 1 g resorcinol, 6.5 ml dimethyl sulfide and a PTFE- coated magnet. The chamber was cooled to −80° C. in a dry ice-ethanol bath. Hydrofluoric acid (HF) (final volume 10 ml) was then admitted to the chamber, which was then kept at 0° C. for 120 min on a magnetic stirrer. The acid was then removed using a water aspirator. The chamber was once again cooled to −80° C. and 10 ml HF were admitted to the chamber, which was placed over a magnetic stirrer at 0° C. for 45 min. The acid was again removed using a water aspirator, and the remaining mixture transferred to a sintered glass filter. The resin/-peptide mixture was then washed with 100 ml 10% (v/v) acetic acid and then with 50 ml diethyl eter. The acetic acid wash was also washed with 50 ml diethyl ether in a separatory funnel, and the ether phase removed from the aqueous phase. The pooled ether washes and the acetic acid wash were then evaporated and lyophilised, respectively, and the peptide product recovered. The peptide was recovered from the aqueous phase only.

The crude product was stored in glass vials in a desiccator at room temperature.

Purification of the Synthetic Peptide

The various components of the crude synthesis product were resolved by applying them to a reverse-phase C-18 silica high-pressure chromatography column using acetonitrile/$H_2O$ (0.1% v/v Trifluoroacetic acid (TFA)) as the mobile phase. 20 μg- 100 mg of the crude peptide were dissolved in up to 1 ml $H_2O$ (0.1% TFA), centrifuged and injected into a 1 ml loop on a Rheodyne (California, USA) HPLC injector. The solution was pumped through a custom-packed 10×500 mm Oligosil reverse-phase C-18 column (Skandinaviska Genetec, Sweden) using a 2152 gradient controller and two 2150 HPLC pumps (LKB, Sweden). The gradient was linear from 0–100% acetontrile in 60 min. The flow rate was 2 ml/min. The elution of the synthesis product was monitored at 206–238 nm using an LKB 2131 variable wavelength absorption monitor. Fractions were collected by hand and repurified if necessary by lyophilisation of the relevant fractions, redissolution and repeating of the chromatographic procedure. The final product was lyophilised and stored in glass vials at −20° C.

PREPARATION OF PEPTIDE ANTIGEN FOR IMMUNOASSAY

The above synthesized peptide was coupled to a carrier, i.e. bovine serum albumin (BSA) in the following manner to form a peptide antigen (coating antigen) which was used in ELISA.

One mg of peptide and 3.6 mg of BSA were dissolved in 2.0 ml of phosphate buffered saline (PBS), pH 7.4.

To this solution, 30 microliters of a 2.5% (w/v) aqueous glutardialdehyde solution was added.

The reaction mixture was incubated at room temperature (20°-25° C.) for one hour, stopped by the addition of 0.5 ml of a 5 M aqueous ethanolamine solution and then dialyzed against one liter of PBS at +4° C. for four hours, with changes of the dialysing fluid after 30 minutes and after two hours.

Next the content of the dialysis bag was gelfiltrated through a column (2.5×60 cm) containing Sephacryl® S-300 gel (Pharmacia, Uppsala, Sweden) equilibrated with PBS. Fractions of 3.0 ml were collected.

Fractions containing coupled material were pooled and the pooled material was used in ELISA as coating antigen and was added directly, without any previous dilution, to the microplate.

ENZYME-LINKED IMMUNOSORBENT ASSAYS (ELISA:s)

Bellow follows a general description of the ELISA:s. The conjugate and the dilution of the conjugate, and the time elapsed before the microplates were read may vary between the various assays. The differences are given after the general description.

GENERAL DESCRIPTION OF ELISA EQUIPMENT

Microtitreplates (Dynatech, mod. nr 129B).
Antigen for coating of microplates (e.g. peptides and proteins).
Coatingbuffer: Phosphate buffered saline (PBS). Incubation buffer: PBS+0.05% Tween 20 (v/v) Aqueous washing fluid: 0.9% NaCl+0.05% Tween 20 Serum (e.g. human and animal reference and test sera) Conjugate (e.g. alkaline phosphatase conjugated swine anti-human IgG antibodies (Orion Diagnostica) and goat anti-rabbit Ig antibodies (Sigma).
Enzyme substrate: p-nitrophenylphosphate tablets (Sigma), 1 mg/ml of substrate buffer (c.f. below) Substrate buffer: 1 M aqueous diethanolamine, pH 9.8, +0.5 mM $MgCl_2$+0.02% $NaN_3$. Pipettes and testtubes

PERFORMANCE
1. Coating of microplates.
Microplates were incubated with 0.1 ml of antigen in PBS at room temperature (20°-25° C.) over night.

2. Incubation with bovine serum albumin (BSA) and serum. The plates were washed four times and then incubated with 0.1 ml of 1% (w/v) BSA in PBS at 37° C. for one hour. After washing, 0.1 ml of serum appropriately diluted in incubation buffer, was added to the wells and the plate(s) was incubated at room temperature for one hour.

3. Incubation with conjugate. After washing, 0.1 ml of conjugate appropiately diluted in incubation buffer, was added to the wells and the plate(s) was incubated at room temperature for two hours.

4. After washing, 0.1 ml of the enzyme substrate solution was added to the wells. The plates were kept at room temperature and the absorbance at 405 nm was read after the time indicated below.

SPECIFIC DESCRIPTIONS OF ELISA ENZYME-LINKED IMMUNOSORBENT ASSAYS

Enzyme-linked immunosorbent assay (ELISA) for measuring the reaction between the synthetic peptide and antibodies in rabbit or human sera, or the reaction between the synthetic peptid and conjugate only.

The peptide used as coating antigen in the ELISA was first treated as described under "Preparation of peptide antigen for immunoassay".

The serum samples were from two different rabbits (rabbit 1 and rabbit 2) and from one human (human 1) and from a pool of human sera from different individuals (human 2). The sera were used at a 1/500 dilution. The conjugate used was an alkaline phosphatase goat anti-rabbit Ig conjugate (Sigma) diluted 1/500 or an alkaline phosphatase swine anti-human IgG conjugate (Orion Diagnostica) diluted 1/100.

The plates were read at times indicated below in an automated ELISA-reader (Titertek, Multiscan).

The results were as follows:

| Serum | Conjugate | Plates read after | Absorbance at 405 nm |
|---|---|---|---|
| Rabbit 1 | goat anti-rabbit | 3 min | 1.21 |
| Rabbit 2 | goat anti-rabbit | 3 min | 1.05 |
| Human 1 | swine anti-human | 20 min | 1.11 |
| Human 2 | swine anti-human | 20 min | 1.26 |
| none | goat anti-rabbit | 5 min | 1.23 |
| none | swine anti-human | 13 min | 0.84 |

Since the above given results in all instances showed positive reactions these data support that the synthesized peptide reacts with both rabbit and human sera—in this latter instance both with serum from one individual (human 1) as well as with a pool of human sera (human 2)—and/or in these instances used alkaline phosphatase goat anti- rabbit Ig conjugate and alkaline phosphatase swine anti-human IgG conjugate, respectively.

That the synthesized peptide reacted with and bound to the respective conjugate was further shown by the ability of the conjugates alone to bind the peptide. That this binding not was caused by interaction of the peptide with alkaline phosphatase in these conjugates was proven in a similar experiment where enzyme alone was used and no binding was observed.

SPECIFIC BINDING OF THE SYNTHESIZED PEPTIDE TO HUMAN IgG

The ability of the synthesized peptide to specifically bind to human IgG was further shown in the following experiment.

The synthesized peptide (0.5 mg) was applied onto a Sepharose® 4 B (Pharmacia, Uppsala, Sweden) column. The CNBr-activated Sepharose® 4 B gel (10 ml) previously had been reacted with an excess (800 mg) of human IgG over night at room temperature to immobilize the IgG through covalent linkage. 150 mg of the human IgG was found to be covalently attached to the gel matrix.

Approximately 85% of the synthesized peptide was retained, i.e. bound to this column at pH 7.2 in PBS at 4° C. as well as at 25° C. The fraction of the synthesized peptide that did not bind to the column most likely comprises contaminants, i.e. peptides of other sequences, which are well-known to occure when peptides are synthesized according to Merrifield.

In a control experiment only utilizing Sepharose® 4 B gel (10 ml) in the column the CNBr activated sites were blocked with ethanolamine (2 ml, 1 M ethanolamine +10 ml PBS) at room temperature over night.

Then the synthesized peptide (0.5 mg) was applied onto the column and the column was irrigated with PBS. All of the synthesized peptide was recovered from the eluate.

Hence the peptide did not bind to Sepharose® 4 B as such but to the human IgG bound to the Sepharose® 4 B gel.

By using such a column (i.e. Human IgG Sepharose® 4 B) it is possible to fractionate the active peptide(s) from the inactive peptide(s).

The active peptide fraction could be eluted from the column by addition of 1% (v/v) aqueous acetic acid. The thus eluted peptide(s) could after restoring to pH 7.2 again be shown to bind to the same column.

Taken together these experiments further support that the synthesized peptide indeed bound to human IgG in the above desribed ELISA experiments.

ASSAY FOR LYMPHOCYTE OR THYMOCYTE PROLIFERATING ACTIVITY: LAF ASSAY

In this experiment the synthesized peptide according to the invention is shown to exhibit a lymphocyte or thymocyte proliferating activity which is comparable to that exhibited by a well-known mitogen, i.e. phytohaemagglutinin.

Substances and Equipment Used in the Assays

| Medium: |
| --- |
| 90 ml RPMI Medium, Flow Laboratories |
| 10 ml Fetal calf serum, Sigma, USA |
| 2 ml Aqueous L-Glutamine solution 14.6 g/l, Sigma, USA |
| 1 ml Sodium pyruvate (100 mM), Gibco Limited, UK |
| 1 ml Penicillin-Streptomycin (10000 units/ml), Gibco Limited, UK |

Mitogen: Phytohaemagglutinin, PHA HA16 2 mg/5 ml $H_2O$, Wellcome Diagnostics (Methyl, 1',2'-$^3$H)-Thymidine: 4.44 Bq/nmol, 120 Ci/mmol, Amersham International plc, UK Gas: air including 4% $CO_2$, Grundgas B-stand. OTC-20, AGA, Sweden Centrifuge: IEC clinical centrifuge, 603 B Climate chamber: WEDCO Incorporated, EZ-17MM Incubation plates: NUNCLON Delta, InterMed, Denmark Cell harvester: Dynatech, Automash 2000

Scintillation counter: Beckman LS-100C liquid scintillation system

Scintillation liquid: OptiPhase MP, LKB produkter AB, Sweden

Description of the Procedure

All the procedures were performed under sterile conditions.

The spleen was removed from a NMRI mouse and was placed in 5 ml of medium at room temperature. Then the spleen was homogenized through a 100 mesh wire net. The homogenate was allowed to settle 2 min and the suspension was decanted from the sediment, whereupon the cells were centrifuged 8 min at 1220 rpm. The supernatant was discarded and the cells were washed once again by suspending in 5 ml medium and centrifugation 8 min at 1220 rpm. The supernatant was discarded and the cells were suspended in 5 ml of medium. The cells were diluted 1/100 and counted in a Bürker chamber, and were then diluted to a final concentration of $5 \times 10^6$ cells/ml.

LAF-Assay

The outer rows of wells in the incubation plates were not used for samples but were filled with 200 μl medium in order to create a stabile temperature zone. "Negative" controls were placed in 12 wells/plate and consisted of 100 μl medium and 100 μl cell suspension. 100 μl samples were placed in new wells and a 1:2 serial dilution was made in the remaining wells of the plate. At least triplicates of the samples were made. As a reference (control) the mitogen phytohaemagglutinin (PHA) was used. Into separate wells were added in triplicate 2.5 μg, 5 μg and 7 μg of PHA in medium as well as 1 μg and 10 μg of the synthesized peptide according to the invention in medium.

The plate was placed in a desiccator having distilled water at the bottom, whereupon the air in the desiccator was replaced by the above mentioned gas in 2 min. The lid was placed onto the desiccator, whereupon the desiccator was placed in the climate chamber and incubated at 37° C., 37% humidity for 48 hours. After the incubation 25 μl of $^3$H-thymidine was added to each well (0.010 μCi/well) and the plate was further incubated 16 hours in the climate chamber.

Then the wells were quantitatively harvested by means of the cell harvester and the test samples were collected on filter paper. To ensure complete harvest of the cells the wells were washed three times with 0.9% (w/v) aqueous sodium chloride solution. The thus harvested cells on filter paper were stamped out and placed into scintillation vials. 6 ml scintillation liquid was added to each vial. The vials were agitated and were allowed to stand for 15 min prior to measurement of the radioactivity in the scintillation counter for 5 min/vial.

| | Results: |
| --- | --- |
| Additions | cpm (range of triplicates) |
| No mitogen | 600–870 |
| PHA 2.5 μg | 6700–8100 |
| PHA 5 μg | 9800–10400 |
| PHA 7 μg | 7000–8100 |
| The peptide of invention: | |
| 1 μg | 3000–4200 |
| 10 μg | 7000–8500 |

The above results clearly show that the synthesized peptide according to the invention exhibits a thymocyte proliferating activity which is similar to that exhibited by the well-known mitogen PHA.

Immunization with the Synthetic Peptide

Enzyme-linked immunosorbent assay (ELISA) for measuring the reaction between native toxin and antibodies specifically induced by immunization of mice with the synthetic peptide according to the invention.

The peptide used as antigen for immunization of mice was first treated as described under "Preparation of peptide antigen for immunoassay".

Groups of mice (NMRI) were immunized subcutaneously with three doses one month apart, 3×0.5 ml, of the peptide antigen using aluminium hydroxide as carrier. Serum samples were collected two months after the third dose. Microplates for ELISA were coated with purified pertussis toxin at a concentration of 1 μg/ml. Gelatin (1%) was used for blocking unspecific binding instead of BSA (c.f. "GENERAL DESCRIPTION OF ELISA"). The endpoint titre of the sera was determined by ten two-fold dilutions starting from a 1/20 dilution and using an absorbance value of 0.1 as cut off. The conjugate used was an goat-anti mouse IgG conjugate (Sigma) diluted 1/500.

The plates were read after 30 minutes in an automated ELISA reader (Titertek, Multiscan).

The results from the assay were as follows:

| | No | Responders | Mean Titre | Range |
|---|---|---|---|---|
| The synthetic peptide | 17 | 15 | 2334 | 320–40960 |
| Control | 12 | 0 | 67 | 20–160 |

It is evident from the above results that the synthetic peptide according to the invention is capable of inducing antibodies upon immunization, which have a clearly higher absorbance with the postvaccination samples than with the prevaccination samples. Thus the tested peptide functions as an antigen and induces antibodies against pertussis toxin.

As a consequence it can be established that the toxin specifically binds to antibodies induced by the synthetic peptide in postimmunization serum samples from mice.

Furthermore the same mice were challenged with purified pertussis toxin (20 μg/mouse=5×$LD_{50}$) and the mean days of survival was investigated in relation to the endpoint titre.

| Number of Mice | Days of survival (mean) | Endpoint titre |
|---|---|---|
| 17 | 3.765 | 80–40960 |
| 15 | 4.000 | 320–40960 |
| 14 | 3.929 | 640–40960 |
| 10 | 4.600 | 1280–40960 |
| 8 | 4.875 | 2560–40960 |
| 6 | 5.333 | 5120–40960 |

-continued

| Number of Mice | Days of survival (mean) | Endpoint titre |
|---|---|---|
| 3 | 6.333 | 10240–40960 |
| Control 12 | 3.333 | |

As is evident from the above Table that the mean survival time increases with higher endpoint titres. The mice having high titres of antibodies are thus partially protected against the challenge.

I claim:

1. A polypeptide of the formula

H—$X^1$—Gln—Thr—Arg—Ala—Asn—Pro—As-
n—Pro—Tyr—Thr——Ser—Arg—Ar-
g—Ser—Val—Ala—Ser—$X^2$—Y in which $X^1$ and $X^2$ each represent either no amino acid or an amino acid which facilitates coupling to a carrier, and Y represents —OH or —$NH_2$.

2. An artificial compound in free or carrier--associated form which binds to glyco-conjugates, characterized in that it is chosen from the group consisting of the polypeptide of the formula H—$X^1$—Gln—Thr—Arg—Ala—Asn—Pro—As-
n—Pro—Tyr—Thr——Ser—Arg—Ar-
g—Ser—Val—Ala—Ser—$X^2$—Y in which $X^1$ and $X^2$ each represent either no amino acid or an amino acid which facilitates coupling to a carrier, and Y represents —OH or —$NH_2$; and functional analogues and functional derivatives of said polypeptide which bind to glyco-conjugates by possessing essentially the same binding conformation in aqueous solution as said polypeptide.

3. An artificial compound in free or carrier--associated form which binds to immunoglobulins, characterized in that it is chosen from the group consisting of the polypeptide of the formula H—$X^1$—Gln—Thr—Arg—Ala—Asn—Pro—As-
n—Pro—Tyr—Thr——Ser—Arg—Ar-
g—Ser—Val—Ala—Ser—$X^2$—Y in which $X^1$ and $X^2$ each represent either no amino acid or an amino acid which facilitates coupling to a carrier, and Y represents —OH or —$NH_2$; and functional analogues and functional derivatives of said polypeptide which bind to immunoglobulins by possessing essentially the same binding conformation in aqueous solution of said polypeptide.

* * * * *